Jan. 2, 1968 D. M. RIVERS Plant Pat. 2,785
PLUM TREE
Filed July 29, 1966
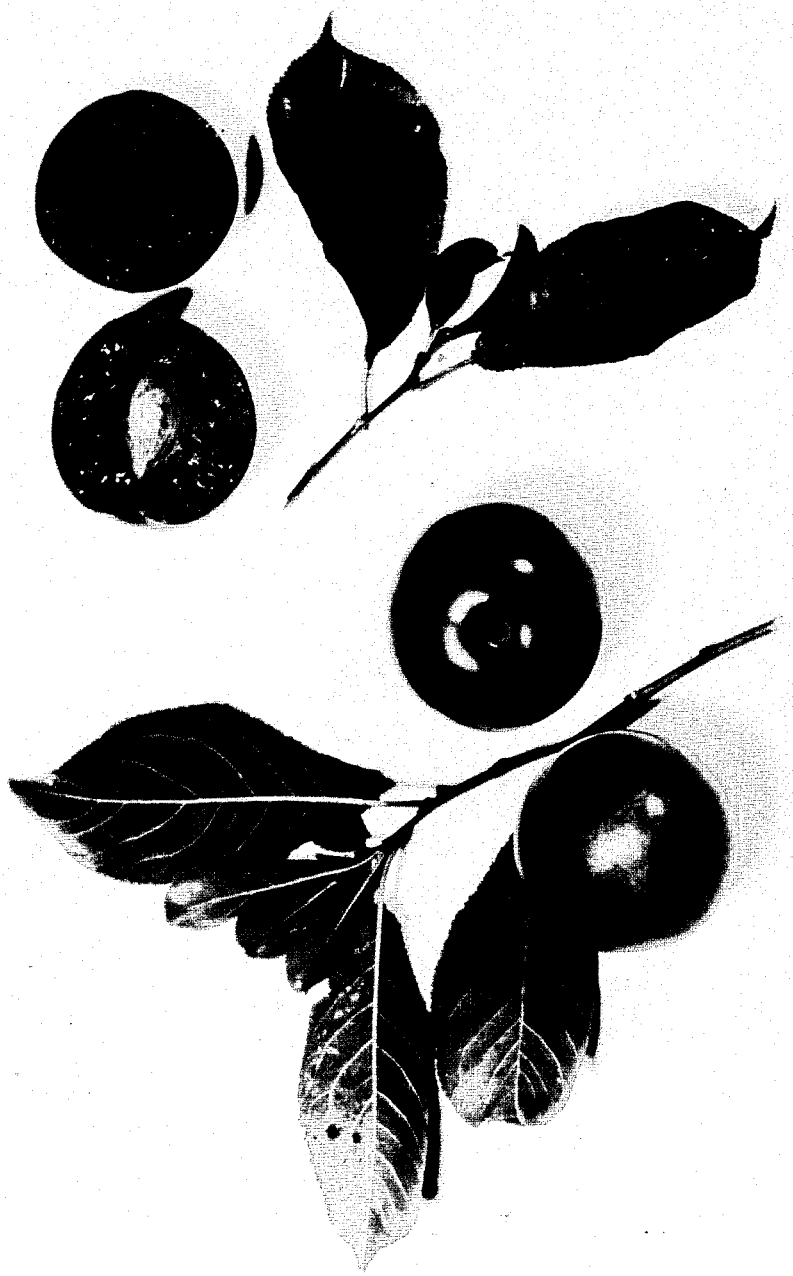
INVENTOR.
DANIEL M. RIVERS
BY Bailey & Dority
ATTORNEYS United States Patent Office Plant Pat. 2,785
Patented Jan. 2, 1968

2,785
PLUM TREE

Daniel M. Rivers, 205 E. Faris Road,
Greenville, S.C. 29605

Filed July 29, 1966, Ser. No. 568,993
1 Claim. (Cl. Plt.—38)

This invention relates to a new and distinct variety of plum tree most closely resembling the Burbank (unpatented).

The new tree is similar to the Burbank in growing qualities, leaves, sturdy limbs, type of bloom and time of blooming, but differs therefrom in that the fruit of the new tree is firm but smooth, and has superior flavor and eating qualities even at shipping stage. The exterior color and color of the flesh also differ.

The tree is characterized especially, in comparison to the Burbank, by the desirable attributes of the tree and fruit having heavy blooming, large white blooms, about the same size as Burbank blooms; heavy fruiting; resistance of the fruit to rot; firm texture of the flesh and medium heavy skin; and what appears to be excellent shipping qualities of the fruit. As to the claim that the seedling has good resistance to brown rot, for three consecutive years tests were made. The first year of test, 1964, three sprays were used and no brown rot was noticed. In 1965 no spray was used and approximately 15% of the plums were lost to brown rot. In 1966, only one was used and less than 1/10 of 1% of brown rot was observed.

I discovered the present variety of plum tree on my small, cultivated orchard located at 205 E. Faris Road, Greenville, S.C., as a chance seedling with several other seedlings from the same tree, labeled when purchased as "Jap Gold" (unpatented), in 1958. This parentage is assumed because the seedlings occurred under the tree referred to. The chance seedling produced fruit in 1961, and the tree and fruit were found to have the desirable characteristics set forth above. During the year 1961, I caused one tree to be asexually reproduced by bud grafting and the resulting tree grew and bore fruit true to form in the year 1966. Such tree was grafted at the Clemson University Experimental Orchard, which is located eight miles east of the Campus of Clemson University in Anderson County, near Pendleton, S.C. The date of first picking was July 3rd and the date of last picking was July 18th of the year 1966. The data given below resulted from observations made at the Clemson University Experimental Orchard in the year 1966.

The accompanying drawing is in the form of a color photograph of characteristic twigs of the new plum tree, together with mature fruit and also shows a fruit of the new variety divided to reveal flesh coloration and pit characteristics.

Referring more specifically to the pomological details of this new and distinct variety of plum tree, the following has been observed under the climatic conditions prevailing at the Clemson University Experimental Orchard. All color plate identifications are by reference to the Munsell Book of Color, pocket edition.

Tree: Size—large and vigorous.
Trunk: Dark brown, medium size, prominent lenticels.
Leaves:
- *Length.*—4".
- *Width.*—1⅞".
- *Form.*—Lanceolate obovate; apex acute, base nearly obtuse.
- *Color.*—Dark green.
- *Vein color.*—5GY 8/2.
- *Margin.*—Finely serrate.
- *Petiole.*—½" long, medium thick.
- *Deciduous.*—Holds leaves to and after first frost.
- *Glands.*—2404—globose, green, to brown color at base of blade.

Flowers: Large white blooms occurring about the middle of March.
Fruit:
- *Maturity when described.*—Ripe July 15, 1966.
- *Size.*—1⅞–2" axial length. Same for width suture plane.
- *Form.*—Round to slightly ovate.
- *Suture.*—Inconspicuous line, from cavity to apex.
- *Ventral surface.*—Rounded.
- *Cavity.*—Very narrow, medium deep, skin does not tear.
- *Base.*—Rounded.
- *Apex.*—Rounded.
- *Stem.*—Short.
- *Length.*—½".
- *Diameter.*—1/16".
- *Adherence to stone.*—Breaks free without tearing.

Skin:
- *Tendency to crack.*—None.
- *Color.*—5R 3/6—overcolor; 10Y 5/4—undercolor.
- *Down.*—None.

Flesh:
- *Color.*—2.5R 3/10; deep burgundy.
- *Surface of pit cavity.*—Deep burgundy, uniform color throughout.
- *Juice.*—Abundant.
- *Texture.*—Fine.
- *Fibers.*—Non-fibrous.
- *Ripens.*—Evenly.
- *Flavor.*—Slightly acid, sweet.
- *Eating quality.*—Very good.

Stone:
- *Type.*—Cling; adheres to flesh over entire surface.
- *Fibers.*—Not noticeable; short.
- *Form.*—Oval.
- *Base.*—Pointed, slightly grooved.
- *Hilum.*—Oval.
- *Apex.*—Short, acute point, about 1/16" long.
- *Sides.*—Symmetrical.
- *Surface.*—Smooth, except furrowed towards the base.
- *Ventral edge.*—Thick, grooved full length.
- *Dorsal edge.*—Sharp, thin.
- *Color of stone.*—10R 6/8.
- *Size.*—Length, 15/16"; width, 9/16"; thickness, 5/16".
- *Tendency to split.*—None.

Use: Shipping and dessert.
Keeping quality: Very good.
Shipping quality: Excellent.

Although the new variety of plum tree possesses the above described characteristics under the growing conditions prevailing at the Clemson University Experimental Orchard, it is to be understood that variation of the usual magnitude in characteristics incident to the growing conditions, fertilization, pruning, and pest control are to be expected.

Having thus described and illustrated my new variety of plum tree what is claimed is:

1. A new and distinct variety of plum tree substantially as illustrated and described which is characterized in comparison to the Burbank especially, by its heavy fruiting, resistance of the fruit to rot, firm texture of the flesh and medium heavy skin of the fruit and excellent shipping qualities of the fruit, excellent eating quality of the fruit even at shipping stage, together with the deep burgundy color of the flesh and deep red color of the skin.

No references cited.

ROBERT E. BAGWILL, *Primary Examiner.*